(12) United States Patent
Beaulieu et al.

(10) Patent No.: US 7,835,599 B2
(45) Date of Patent: Nov. 16, 2010

(54) FLOW CYTOMETRY ANALYSIS ACROSS OPTICAL FIBER

(75) Inventors: René Beaulieu, L'Ancienne-Lorette (CA); Michel Fortin, Lac-Beauport (CA); Alain Cournoyer, René-Lévesque Est (CA)

(73) Assignee: Institut National d'Optique, Québec (CA)

( * ) Notice: Subject to any disclaimer, the term of this patent is extended or adjusted under 35 U.S.C. 154(b) by 617 days.

(21) Appl. No.: 11/509,584

(22) Filed: Aug. 25, 2006

(65) Prior Publication Data

US 2007/0047868 A1    Mar. 1, 2007

Related U.S. Application Data

(60) Provisional application No. 60/710,865, filed on Aug. 25, 2005.

(51) Int. Cl.
*G02B 6/00* (2006.01)
(52) U.S. Cl. ......................................... 385/12
(58) Field of Classification Search .................. 385/12
See application file for complete search history.

(56) References Cited

U.S. PATENT DOCUMENTS

| | | | |
|---|---|---|---|
| 4,149,867 A * | 4/1979 | Akamatsu et al. ............ 65/417 |
| 4,667,830 A | 5/1987 | Nozaki, Jr. et al. |
| 4,889,407 A * | 12/1989 | Markle et al. ................. 385/12 |
| 5,268,978 A | 12/1993 | Po et al. |
| 5,464,581 A | 11/1995 | Van den Engh |
| 5,483,469 A | 1/1996 | Van den Engh et al. |
| 5,579,429 A * | 11/1996 | Naum ........................ 385/143 |
| 5,602,039 A | 2/1997 | Van den Engh |

(Continued)

FOREIGN PATENT DOCUMENTS

CA    2004250    3/1994

(Continued)

OTHER PUBLICATIONS

Alain Cournoyer, Laser drilling and routing in optical fibers and tapered micropipettes using excimer, femtosecond, and $CO_2$ lasers, as found on Internet website http://adsabs.harvard.edu/cgi-bin/nph-bib_query?bibcode=2004SPIE.5578..596C&.

(Continued)

*Primary Examiner*—Uyen-Chau N Le
*Assistant Examiner*—Hoang Tran
(74) *Attorney, Agent, or Firm*—Ogilvy Renault, LLP

(57) ABSTRACT

A flow cytometer type apparatus and method for analyzing a fluid, where the fluid is fed through a passageway within an optical fiber and the light is guided by the fiber across the passageway and intersects the fluid therein. The apparatus includes an optical fiber with a passageway traversing it, a channeling system to channel the fluid medium within the passageway, a light source to propagate light within the optical fiber and across the passageway, and a detection system for detecting an intensity of the light exiting the fiber. The method includes channeling the fluid medium through the passageway, propagating light within the optical fiber, and detecting an intensity of the light output. Preferably, the fluid includes small bodies, like bacteria which are analyzed by assessing the detected exiting light intensity.

23 Claims, 14 Drawing Sheets

U.S. PATENT DOCUMENTS

| | | | |
|---|---|---|---|
| 5,643,796 A | 7/1997 | Van den Engh et al. | |
| 5,659,644 A | 8/1997 | DiGiovanni et al. | |
| 5,700,692 A | 12/1997 | Sweet | |
| 5,818,981 A | 10/1998 | Pan et al. | |
| 5,912,257 A * | 6/1999 | Prasad et al. | 514/356 |
| 5,983,676 A | 11/1999 | Brown | |
| 6,097,870 A * | 8/2000 | Ranka et al. | 385/127 |
| 6,246,026 B1 | 6/2001 | Vergeest | |
| 6,438,294 B1 | 8/2002 | Lauzon et al. | |
| 6,509,547 B1 | 1/2003 | Bernstein et al. | |
| 6,535,655 B1 | 3/2003 | Hasui et al. | |
| 6,713,019 B2 | 3/2004 | Ozasa et al. | |
| 6,793,642 B2 | 9/2004 | Connelly et al. | |
| 7,324,724 B2 | 1/2008 | Lévesque et al. | |
| 2003/0098421 A1 | 5/2003 | Ho | |

FOREIGN PATENT DOCUMENTS

| | | |
|---|---|---|
| CA | 2321782 | 9/1999 |
| CA | 2204865 | 8/2001 |
| WO | 9801071 | 1/1998 |

OTHER PUBLICATIONS

Yiou et al., "Stimulated Raman scattering in an ethanol core microstructured optical fiber", Optics Express, Jun. 13, 2005, vol. 13, No. 12, OSA.

* cited by examiner

FLOW CYTOMETRY ANALYSIS ACROSS OPTICAL FIBER

CROSS-REFERENCE TO RELATED APPLICATIONS

This application claims priority under 35 USC §119(e) of U.S. provisional patent application No. 60/710,865 filed Aug. 25, 2005, the specification of which being hereby incorporated by reference.

BACKGROUND OF THE INVENTION

1) Field of the Invention

The invention relates generally to the field of flow cytometry. More particularly, the invention relates to methods and systems for studying a fluid channeled within a passageway intersecting the light guided in an optical fiber.

2) Description of the Prior Art

Many techniques exist to study the presence, the quantity, the size or the vitality status (alive or dead) of bacteria or of other small bodies. For example, the number of bacteria may be determined by counting them in a Petri dish, using a microscope counting technique, via the chain reaction of polymerase, and using flow cytometry. Flow cytometry is a technique which allows one to analyze and to sort small bodies like cells, bacteria and other particles in a fluid medium. In flow cytometers of the prior art, a fluid containing the small bodies is circulated within a transparent tube, and a laser is aimed at the tube. The laser light, after having crossed the tube, is received and analyzed, which gives information about the particles flowing within the tube. Several parameters of the particles may be studied simultaneously (the nature of the particle, the dimension of the particle, etc.) by marking the particles to be analyzed with dyes and measuring the fluorescence emitted by those dyed particles and by analyzing the intensity of the transmitted laser light beam after it has interacted with the fluid. All of the above techniques require the intervention of a skilled technician. In particular, in the case of the prior art flow cytometry techniques, a skilled technician must adjust and precisely align the laser beam so that the laser beam may efficiently interact with the particles flowing into the tube.

Known flow cytometers are described, for example, in U.S. Pat. Nos. 4,667,830; 5,464,581; 5,483,469; 5,602,039; 5,643,796; 5,700,692; 6,713,019 and 6,793,642. The flow cytometers, such as described in the patents cited above, usually employ lasers as the light source. Although lasers are generally effective in producing focused beams which are of sufficient intensity to excite the particles of interest to provide detectable fluorescence, the use of lasers can have some drawbacks. For example, the types of lasers employed in many known flow cytometers are very expensive, and thus increase the overall cost of the system. Also, because the lasers emit very high intensity light, stray light from the laser beam can interfere with the fluorescent light emanating from the particles of interest, thus adversely affecting fluorescence measurements. Therefore, a need exists for an improved system to obtain more accurate measurements while also decreasing the overall size and cost of the apparatus.

SUMMARY OF THE INVENTION

An object of the invention is to overcome at least some of the drawbacks of the prior art.

In accordance with a first broad aspect, the invention provides an apparatus for analyzing a fluid. The apparatus comprises: an optical fiber with a core, and a passageway traversing the optical fiber including its core, and in which the fluid is to be channeled; a channeling system adapted to channel the fluid through the passageway; a light source system optically coupled to the optical fiber to propagate light in the core of the optical fiber, and across the passageway; and a light detection system optically coupled to the optical fiber for detecting an intensity of the light exiting the fiber after having propagated across the fluid in the passageway.

Preferably, the apparatus is used for studying small bodies in a fluid medium, and the passageway is a hole defined transversally within the optical fiber. At least one of the small bodies is thus analyzed by assessing the detected exiting light intensity.

In accordance with another broad aspect, the invention provides a method for analyzing a fluid. The method comprises: channeling the fluid through a passageway traversing an optical fiber including its core; propagating light into the core of the optical fiber and across the passageway and generating a light output; and detecting an intensity of the light output to analyze the fluid.

In accordance with still another broad aspect, the invention provides a flow cytometer for analyzing a fluid by channeling the fluid and intersecting the channeled fluid with light for interaction therewith and to be detected thereafter. The flow cytometer being characterized in that the fluid is channeled at least partly transversally through an optical fiber and the light is guided longitudinally within the optical fiber and intersects the channeled fluid.

In accordance with still another broad aspect, the invention provides a flow cytometer type apparatus and method for analyzing a fluid, where the fluid is fed through a passageway within an optical fiber and the light is guided by the fiber across the passageway and intersects the fluid therein. The apparatus includes an optical fiber with a passageway traversing it, a channeling system to channel the fluid medium within the passageway, a light source to propagate light within the optical fiber and across the passageway, and a detection system for detecting an intensity of the light exiting the fiber. The method includes channeling the fluid medium through the passageway, propagating light within the optical fiber, and detecting an intensity of the light output. Preferably, the fluid includes small bodies, like bacteria which are analyzed by assessing the detected exiting light intensity.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
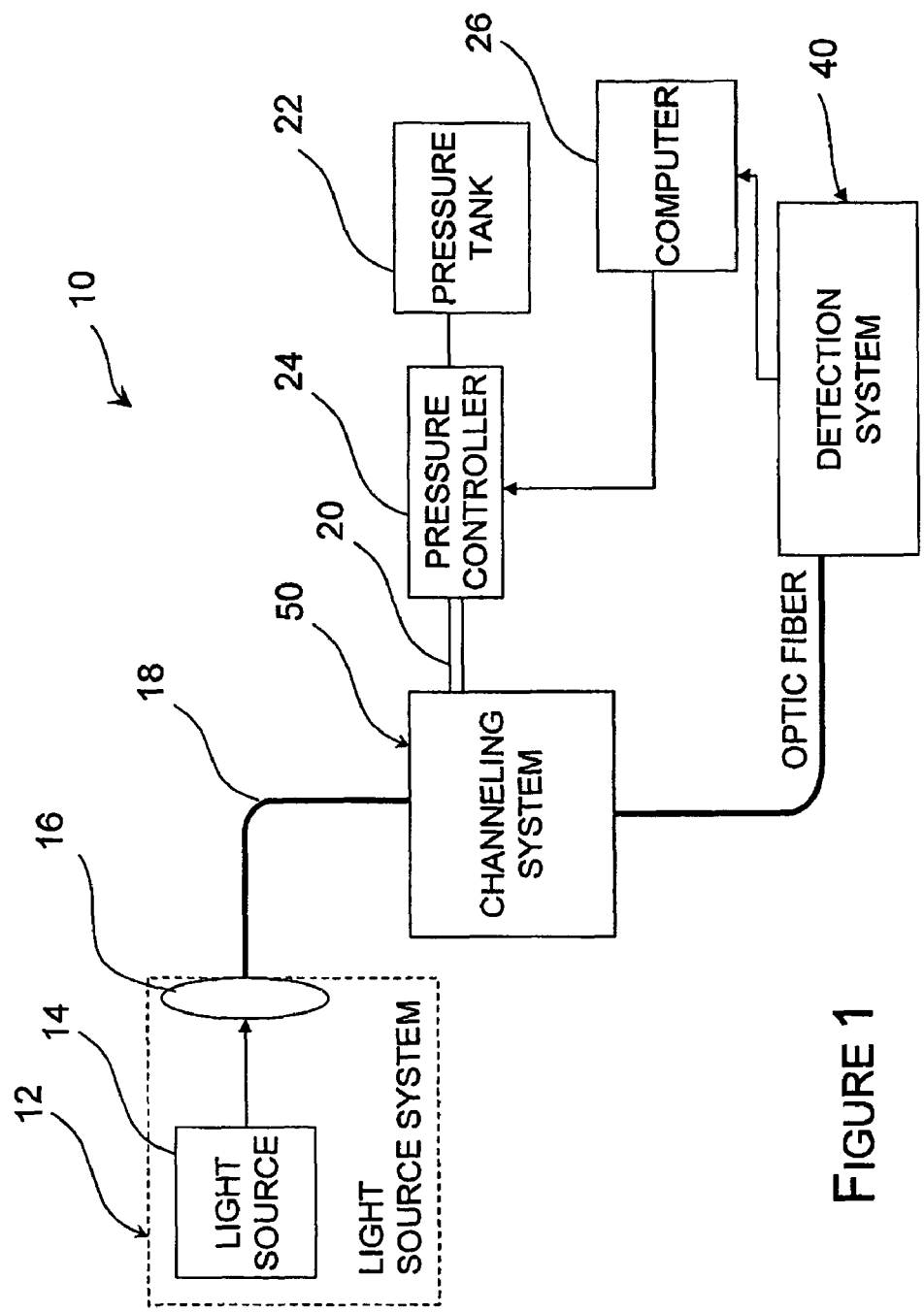
FIG. 1 is a block diagram of the main components of an apparatus for studying a fluid, in accordance with one embodiment of the present invention.
Figure 2:
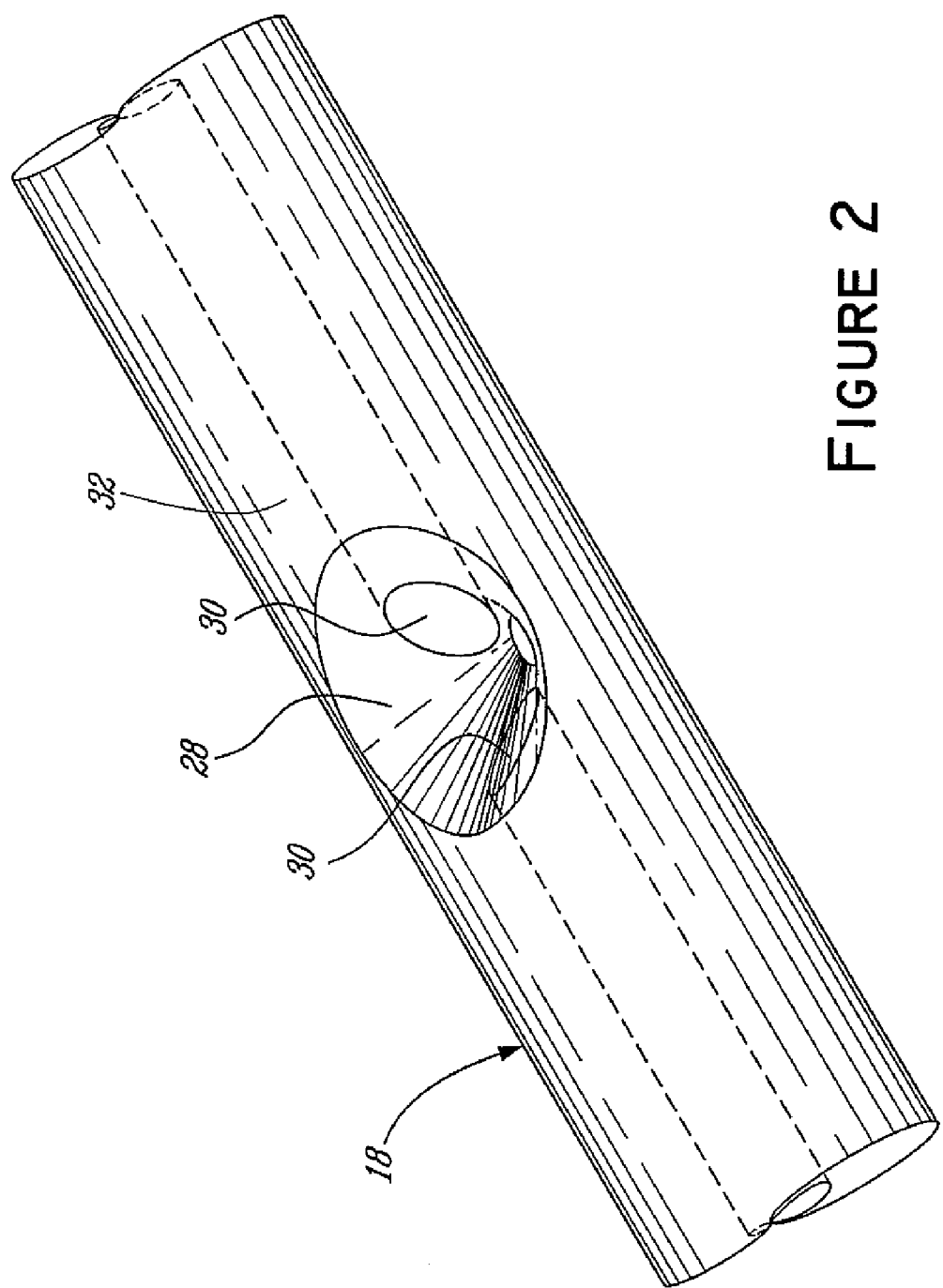
FIG. 2 is a schematic top plan view, fragmented, of an optical fiber with a transversal hole for use in the apparatus of FIG. 1.

FIG. 1 schematically illustrates the main components of an apparatus 10 in accordance with one embodiment of the present invention. A light source system 12, preferably including a light source 14 and an injection lens 16, injects light in an optical fiber 18. The optical fiber 18 has a passageway defined within it, such as a transversal hole 28 depicted in FIG. 2, and the light propagates in the core 30 of the optical fiber 18 and across the transversal hole 28. It is to be noted that FIG. 2 is a schematic view and is therefore not a true representation of the appearance of the transversal hole 28 and the core 30 of the optical fiber. A channeling system 50 channels a fluid through the passageway, where the fluid interacts with the propagating light. In this embodiment, the flow rate of the fluid through the passageway in the optical fiber 18 is controlled by varying its pressure, and thus a pressure inlet 20 is provided to connect the channeling system 50 to a pressure tank 22 via a pressure controller 24, which is preferably controlled by a computer 26. Information about the fluid and its reaction to being traversed by a propagating light is extracted by analyzing the intensity of light exiting the optical fiber 18. A detection system 40 is used to monitor the variation of exiting light intensity with time and to monitor the intensity of light at precise wavelengths, from which the desired information is extracted. The detection system 40 is preferably also connected to a computer, preferably computer 26. Typically, the fluid includes small bodies, and the system is used to study the small bodies within the fluid, but the system can also be used to study a homogeneous solution. In the preferred embodiment, the small bodies are bacteria and the fluid medium is water in which fluorochrome dyes are added.

Instead of being provided as a transversal hole in the fiber, the passageway for the fluid within the optical fiber can be provided alternatively, as will appear to those skilled in the art. For example, the optical fiber could be cut, and the two cut ends can be held spaced apart at a distance allowing light from one cut end to at least partly travel across the passageway thereby defined, and into the other cut end to continue to be guided therein. In order to facilitate this type of passageway, the two cut ends can be partly fused together in order to only create a tubular or differently-shaped channel within the fiber where the fluid will be able to travel. A channel support allowing light to propagate therethrough could also be inserted within the passageway to facilitate fusing of the two cut ends of the fiber while ensuring a specific shape and size for the channel. It will be readily understood that instead of cutting one fiber into two pieces, two fibers could be used and aligned to create the passageway. Other ways of creating the passageway could also be found by one skilled in the art and are intended to be covered by the present invention. For practical reasons, the transversal hole 28 embodiment for the passageway is preferred. Therefore, to simplify the text, the passageway will be referred to as a transversal hole created in the fiber hereinafter.

Figure 3:
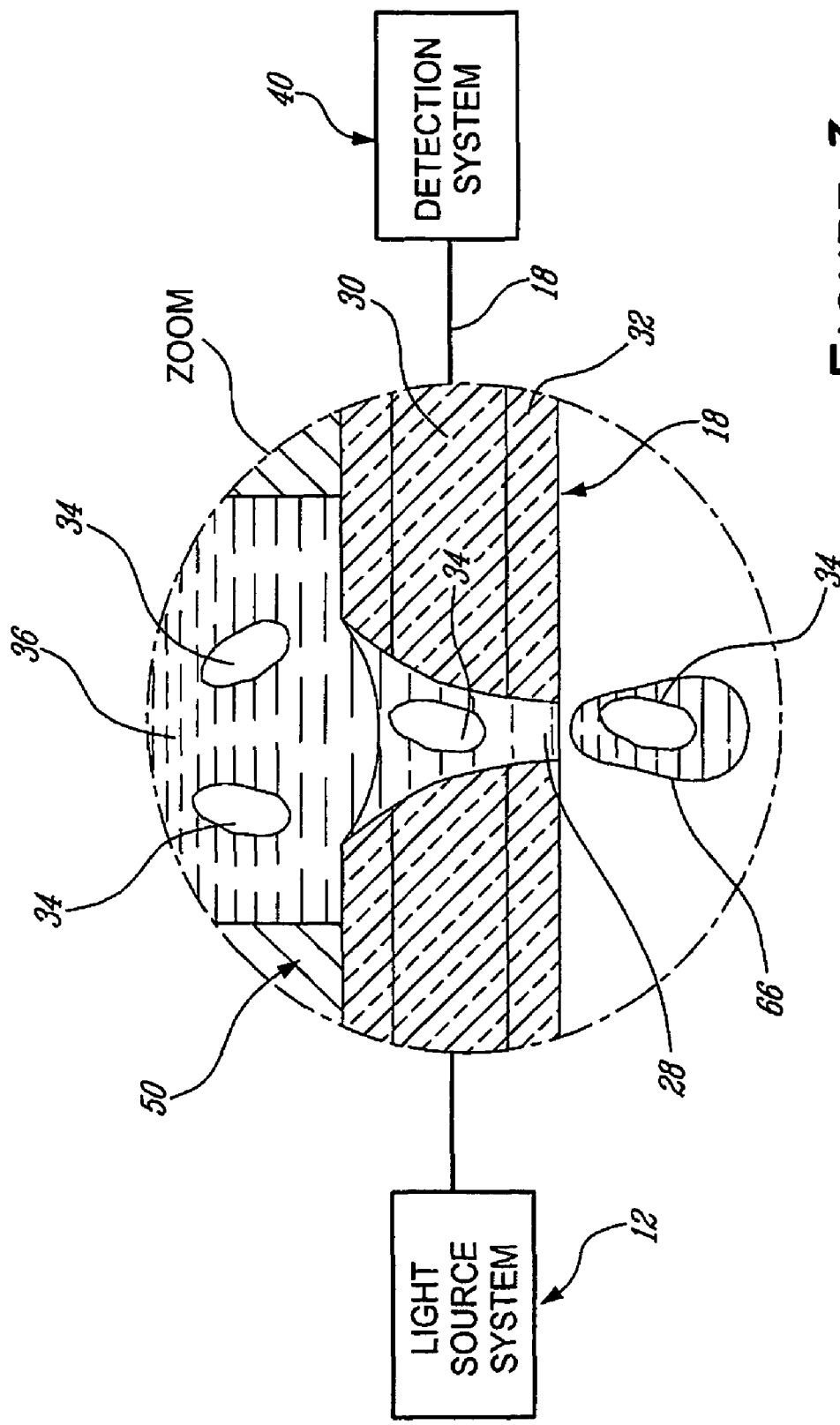
FIG. 3 is a schematic view, partly enlarged, of the intersecting action of a light beam and a small body within the passageway created in the optical fiber of the apparatus of FIG. 1.

The intersection of the light and small bodies in the apparatus 10 is schematically illustrated in FIG. 3, where the portion of the optical fiber 18 having the transversal hole 28 is schematically enlarged. The small bodies 34 in the fluid medium 36 are channeled through the hole 28, and the light propagates in the core 30 of the optical fiber 18. The hole 28 runs through the core 30 and the cladding 32 of the optical fiber 18 in a transversal direction (see also FIG. 2). Preferably, the hole 28 has a slightly frusto-conical shape inclined by of a few degrees relatively to a perpendicular axis to the optical fiber 18 (exaggerated on the Figures). This shape results from the fabrication process and is not essential, it has a negligible effect on light attenuation. When a small body 34 passes in the hole 28, its trajectory intersects the light beam from the light source system 12 which travels within the core 30 of the optical fiber 18 and across the hole. The light intensity exiting the optical fiber 18 is thus modulated due to the interaction of the light with the content of the hole 28. Those modulations are detected with the detection system 40 which allows extracting information about the small bodies 34. In certain applications, fluorescence light is emitted by the small bodies 34 in response to stimulation at the wavelength of the guided light propagating in the optical fiber 18. The fluorescence is partly guided in the optical fiber 18 and can be detected by the detection system 40.

Figure 4:
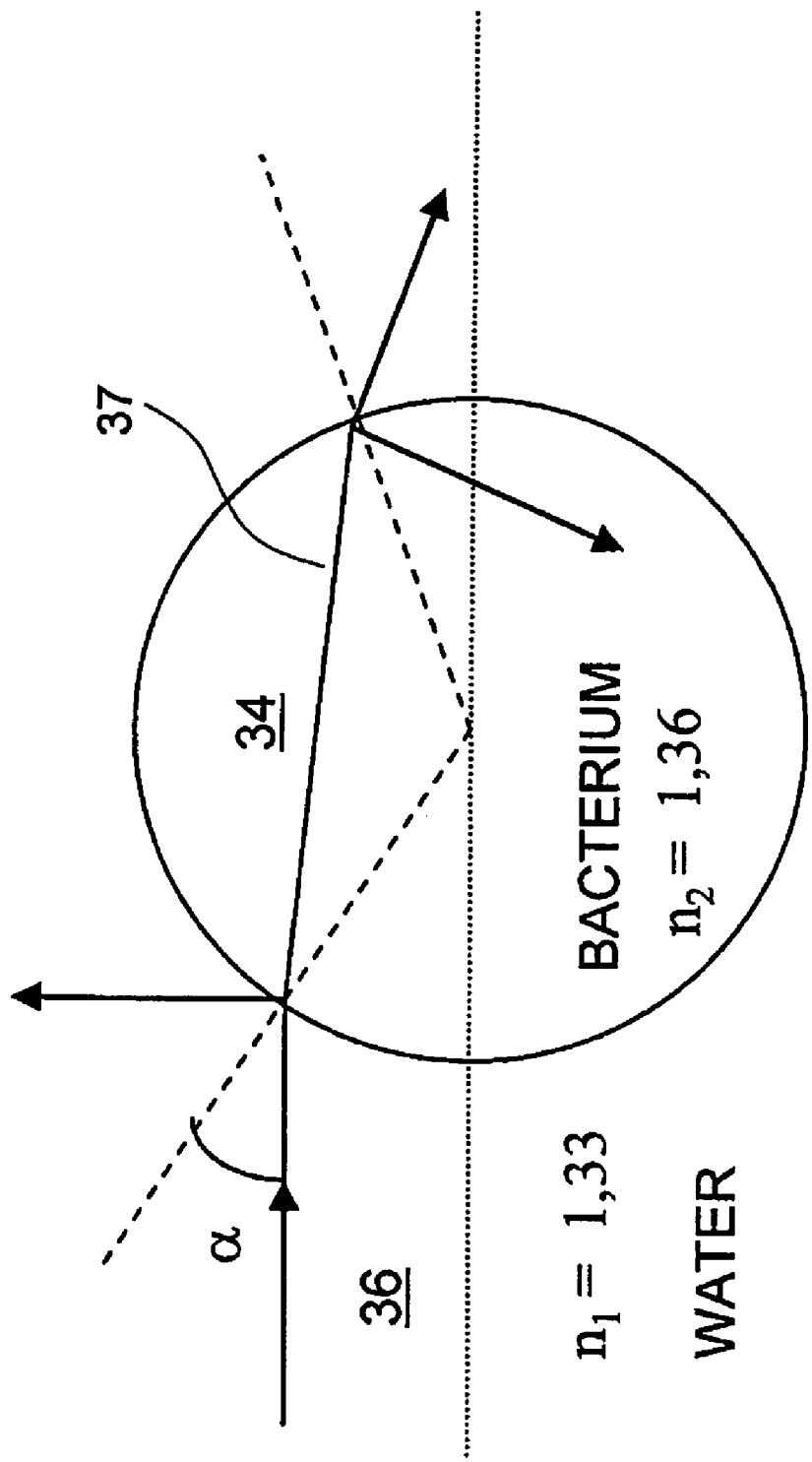
FIG. 4 is a schematic view, enlarged, of the interaction of a ray of light intersecting a small body and being attenuated in the apparatus of FIG. 1.

In one embodiment of the present invention, the apparatus is used to analyze bacteria 34 in a fluid medium 36. The presence or absence of a bacterium 34 within the hole 28 affects the output of light from the optical fiber 18. The interaction between a small body and a ray of light is schematically depicted in FIG. 4. Experimental results from a research team of the Memorial University of Newfoundland show that the refractive index of bacteria is from 3% to 6% higher than the refractive index of water. Hence, when a ray of light 37 crosses a bacterium 34 in the hole, it crosses two surfaces of the bacterium, an entrance and an exit. Due to the difference in the refractive index between the two substances, refraction occurs if the angle of incidence is not of 0 degree, and the direction of the ray is varied. Further, partial reflection also occurs at each surface the ray crosses. The consequence of this is that the intensity of light that successfully crosses the hole is attenuated when a bacterium 34 is present. Also, the attenuation is higher when the bacteria are labeled with fluorophores, as will be discussed further down.

Thus, the output intensity of light exiting the optical fiber 18 carries information enabling to detect the presence or absence of a bacterium 34 in the hole 28. By extending this experimentation over time, with the fluid medium 36 flowing within the hole 28 at a controlled flow rate, it is possible to count the number of bacteria 34 which have passed through the hole. This allows one to study the quantity or density of bacteria 34 in the fluid medium 36. Further, the size of the individual bacterium 34 intersecting the beam will affect the intensity attenuation in the beam. Therefore, with sufficiently precise instruments in the detection system 40, and appropriate algorithms which will be discussed further down, it is possible to measure the attenuation of the light and to evaluate the size of the bacteria 34 in the fluid medium 36. Consequently, when it is desired to obtain information concerning individual bacterium 34, ideal results are obtained when the region of the hole 28 where the bacteria and the light intersect is not much larger than the size of a bacterium 34. The bacteria 34 are then forced to pass across the light beam one by one.

Ideally, a fluid medium having the same index of refraction than the core of the optical fiber is used to maximize the transmission of light. However, the variation of the light intensity resulting from the passage of a bacteria can be amplified, and the absolute value of the intensity is not therefore of utter importance. If fluorescence light intensity is detected, as will be discussed further down, the quantity of light detected diminishes as a function of the difference between the indices of refraction. This diminution relatively to the ideal configuration is generally below 3%, and is thus of little relative importance.

Depending on the application, the size of the hole can be varied between a few to several tens of microns in diameter to accommodate the study of different sizes of small bodies. Typically, in the case of bacteria, the hole has a diameter between 25 and 50 μm. As it is shown in FIGS. 2 and 3, the hole 28 is preferably defined in a transversal orientation relatively to the axis of the optical fiber 18, in order to maximize light propagation across it. The hole 28 is preferably created by laser micro-machining, although other techniques may alternatively be used. Also, in bacterial analysis applications, a common multi-mode optical fiber having a 125 μm outer diameter (of the cladding 32), and a core 30 of 62.5 μm diameter is typically used. However, optical fibers having cores of larger or smaller diameters may alternatively be used.

The invention is adaptable to a variety of alternative applications. Alternative embodiments to the apparatus include using a single mode optical fiber, using optical fibers with a core of different size, using an optical fiber with a different outer diameter, and using a transversal hole of different size or shape. As it is known in the art, the world of optical fibers is evolving rapidly and new types of fibers such as photonic crystal fibers have emerged which do not have the same type of cores and claddings as traditional fibers. Such unconventional fibers may be used if they are determined to be suitable for specific applications. Henceforth, the definition of the term core herewithin is not to be understood as limiting to the traditional meaning of cores, but rather to the region of the fiber wherein the light is guided. Furthermore, optical fibers with core diameters ranging from a few microns to over 200 μm are routinely available. The size of the hole may thus be varied between a few to several hundred microns in diameter to accommodate the study of different sizes of small bodies by selecting an appropriate optical fiber. The alternatives used will typically be selected to enhance transmission characteristics and to adapt the apparatus either to different sizes of small bodies 34 or to different information to be analyzed, the exact choice is thus left entirely to those skilled in the art realizing specific embodiments of the invention subsequently to routine experimentation.

Figure 5B:
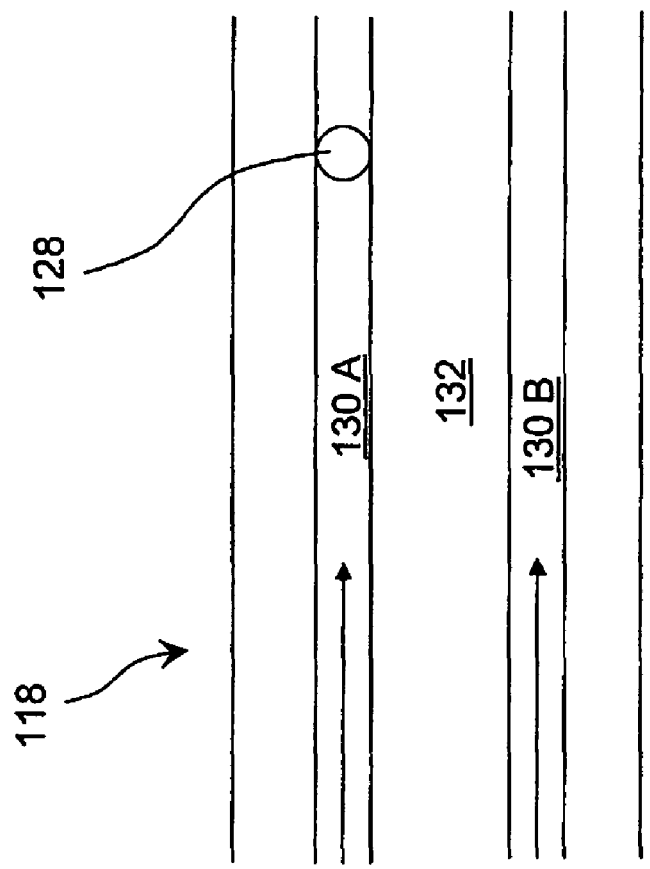
FIG. 5 includes FIG. 5A and FIG. 5B which are front and side cross-sectional views, respectively of an optical fiber with two cores for use in an alternative embodiment of the invention.
Figure 5A:
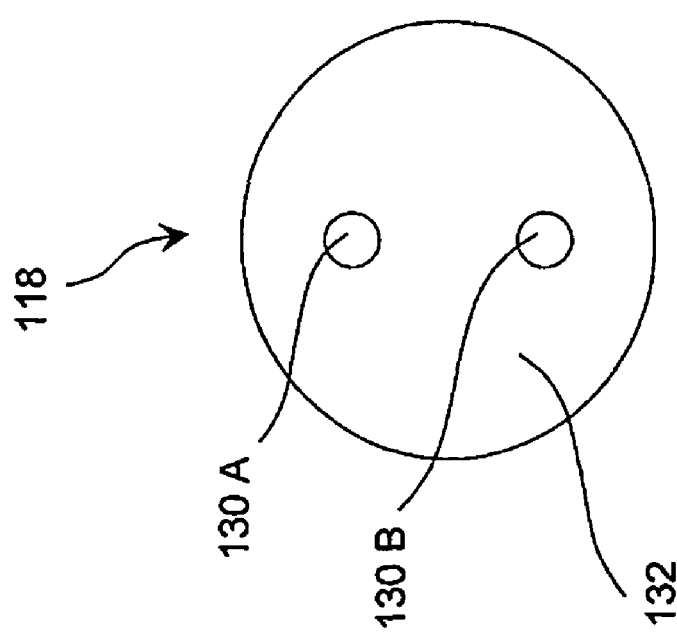

Referring to FIGS. 5A and 5B, an exemplary use of a non-traditional optical fiber is depicted. The double core optical fiber 118 has a first core 130 A and a second core 130 B. A hole 128 in which the fluid medium is channeled is defined transversally to the first core 130A. When the light traveling within the first core 130A encounters a small body in the hole 128, it goes through a phase shift relatively to the one traveling the second core 130B. The difference of phase between the light traveling the first and second cores could be detected by an interferogram created at the exit of the fiber. Since the interferogram created depends on the size of the small bodies, this method of studying small bodies could prove even more precise than in the case of an optical fiber having a single core. Another method involves the monitoring of the light traveling within the second core for measuring the variation of the light source. Such double core optical fibers are available from INO (Institut National d'Optique), Québec, Canada.

Another alternative which could be used is an optical fiber having two claddings (not illustrated). These optical fibers are called Double Clad Optical Fibers (DCOF). DCOF offer the advantage of having a greater numerical aperture than the more traditional single cladding optical fibers and can thus guide a greater intensity of light, which is typically desired with the present invention. They are generally used for high power optical amplifiers or fiber lasers and consist of two concentric waveguides: one for pump and the other for signal wavelength. The core is single mode and has generally a diameter of few micrometers and is surrounded by a glass cladding of few hundreds of micrometer. The core is doped with rare-earth material for amplification of the signal and then guides the light to be amplified. The first cladding is surrounded by a second cladding to guide the pump light. The second cladding is generally of some low index material to provide a high numerical aperture for the pump. The large area and acceptance angle of the pump cladding allow efficient coupling of high power, low brightness pump diodes. A DCOF could be used with a standard core for a better efficiency of excitation and collection of the fluorescence emission coming from small bodies. The single mode core can supply a better irradiance and then produce a more intense fluorescence radiance which can be collected by the first cladding of the DCOF having a high numerical aperture. Since the excitation core is not doped with rare-earth, and is contained in the center of the DCOF, significant reduction in autofluorescence can be reached with the DCOF compared with standard multimode optical fiber with the cladding surrounded by a fluorescent coating such as nylon and tefzel. Double clad optical fibers are also available from INO.

Turning back now to FIG. 3, in some applications where the small bodies 34 are biological specimen containing naturally occurring fluorophores such as riboflavin or NADH (nicotinamide adenine dinucleotide), the small body 34 emits endogenous fluorescence which is stimulated by exposure to light at certain wavelengths, typically in the UV spectrum. This is true for many types of cells and microorganisms. In such cases, a portion of the endogenous fluorescence emitted by the small body could be guided within the optical fiber 18 and be detectable at the exit of the optical fiber 18 by a suitable detection system 40, to provide specific information about the small body 34 under study, especially when a high intensity of light affects the small body 34. In order to generate this fluorescence, use would be made of a Light Emitting Diode (LED) with peak emission within the UV spectrum, and corresponding to the stimulation wavelength, as a light source. In order to acquire information on the status of the small body 34, the light source 14 must be selected adequately and take into account the type of small body 34 to study. Typically, one or more LEDs 14 are used. Preferably, the LEDs 14 are optically coupled to the optical fiber 18 via a known optical injection device such as, for example, a microscope focusing lens assembly. Alternative light sources that can be used include laser diodes, for example.

In one application of the present invention, information as to the vitality state (if it is alive or dead) of bacterium 34 is obtained using the apparatus. The structure and composition of dead bacteria is different from that of live bacteria. For example, the membrane of dead bacteria is generally perforated, and no longer achieves impermeability. The perforated membrane thus allows contact between molecules of specific dyes and internal constituents of dead bacterium. Hence, dyes can be used to color proteins or other nucleic acids in dead bacteria, whereas other dyes have a coating action onto the membrane of living bacteria. Preferably, fluorochrome dyes which emit fluorescent radiation when stimulated at certain wavelengths are used. The preferred dyes are the penetrating action Marina Blue™ dye with stimulation wavelength of 365 nm and fluorescent emission wavelength of 460 nm, and the Prodan™ coating action dye with stimulation wavelength at 355 nm and fluorescent emission wavelength at 525 nm, both available from Invitrogen (www.invitrogen.com). The dyes produce different effects on live and dead cells when submitted to the appropriate UV radiation, and emit fluorescence light at different wavelengths. Part of the fluorescence light emitted is guided in the optical fiber and can be detected at an exit thereof. By studying the spectrum of the light exiting the optical fiber 18, it is thus made possible to determine if the cells are alive or dead. In this specific application, a LED 14 with peak emission at 365 nm and a power of 100 mW is believed to be particularly effective in obtaining the desired fluorescence intensity. Such a LED 14 is available from Nichia American Corporation. Other dyes can alternatively be used in combination with a light source of corresponding wavelengths, for example, a laser diode emitting light in the visible spectrum could be used with fluorochrome dyes which have an absorption wavelength located in the visible spectrum.

Figure 6:
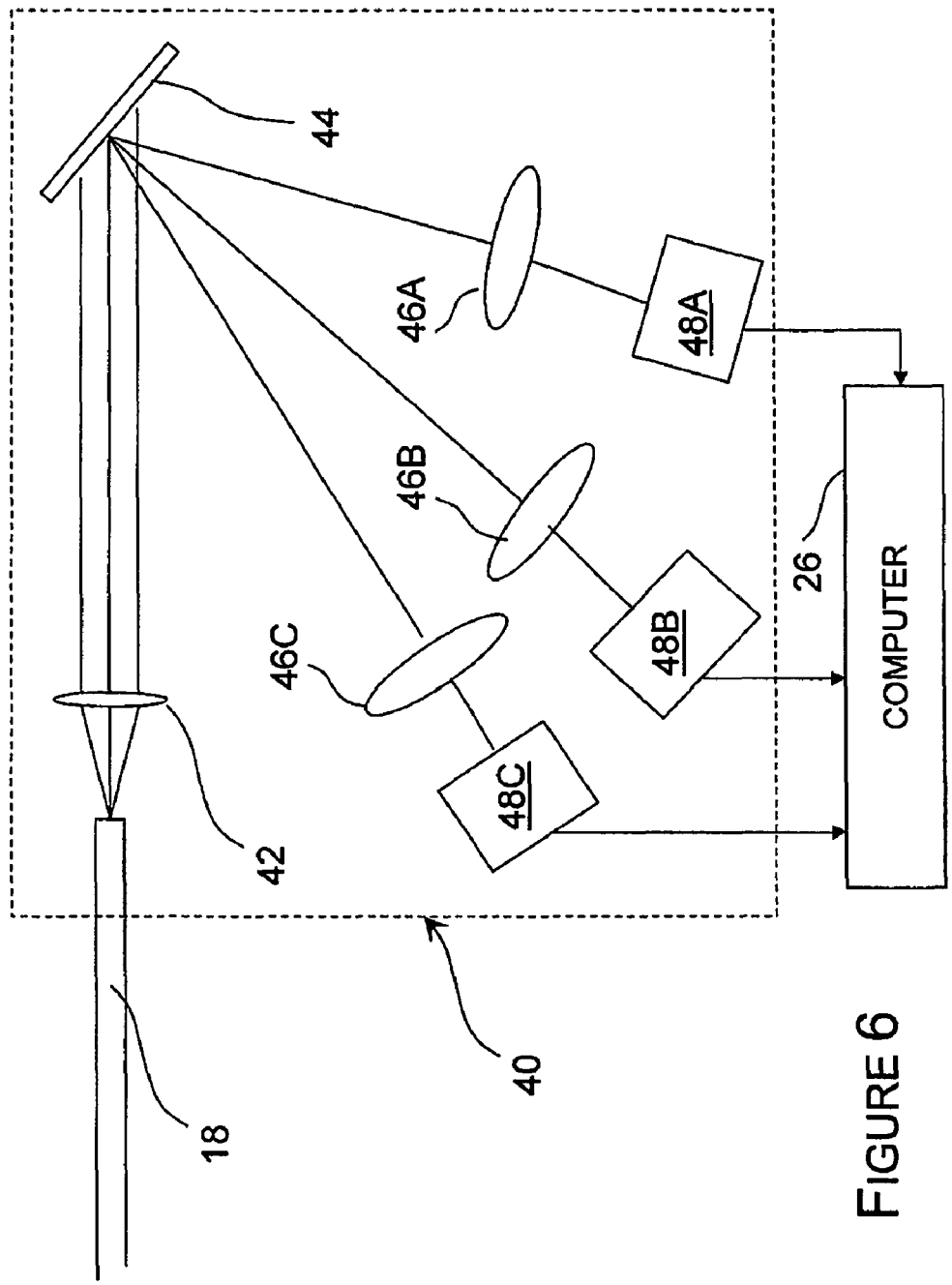
FIG. 6 is a schematic view of a detection system of the apparatus of FIG. 1.

FIG. 6 shows an exemplary embodiment of the detection system 40 (see also FIGS. 1 and 3) adapted to measure the fluorescence signal and detect the vitality status of bacteria. The light exiting optical fiber 18 is fed through a collimation lens 42 and directed to a diffraction grating 44. After diffraction, the intensities at three wavelengths are detected: a fluorescence wavelength A emitted by dead bacteria, a fluorescence wavelength B emitted by living bacteria, and a wavelength C corresponding to the wavelength of the light source (in this case a LED). Each wavelength is diffracted at a different angle by the diffraction grating 44. A first focusing lens 46A and photodetector 48A assembly is used to measure the exiting intensity at wavelength A, a second such assembly is used to measure the exiting intensity at wavelength B, and a third similar assembly is used to measure the exiting intensity at wavelength C. Preferably, the photodetectors 48A, 48B, and 48C are connected to a computer 26.

Figure 7:
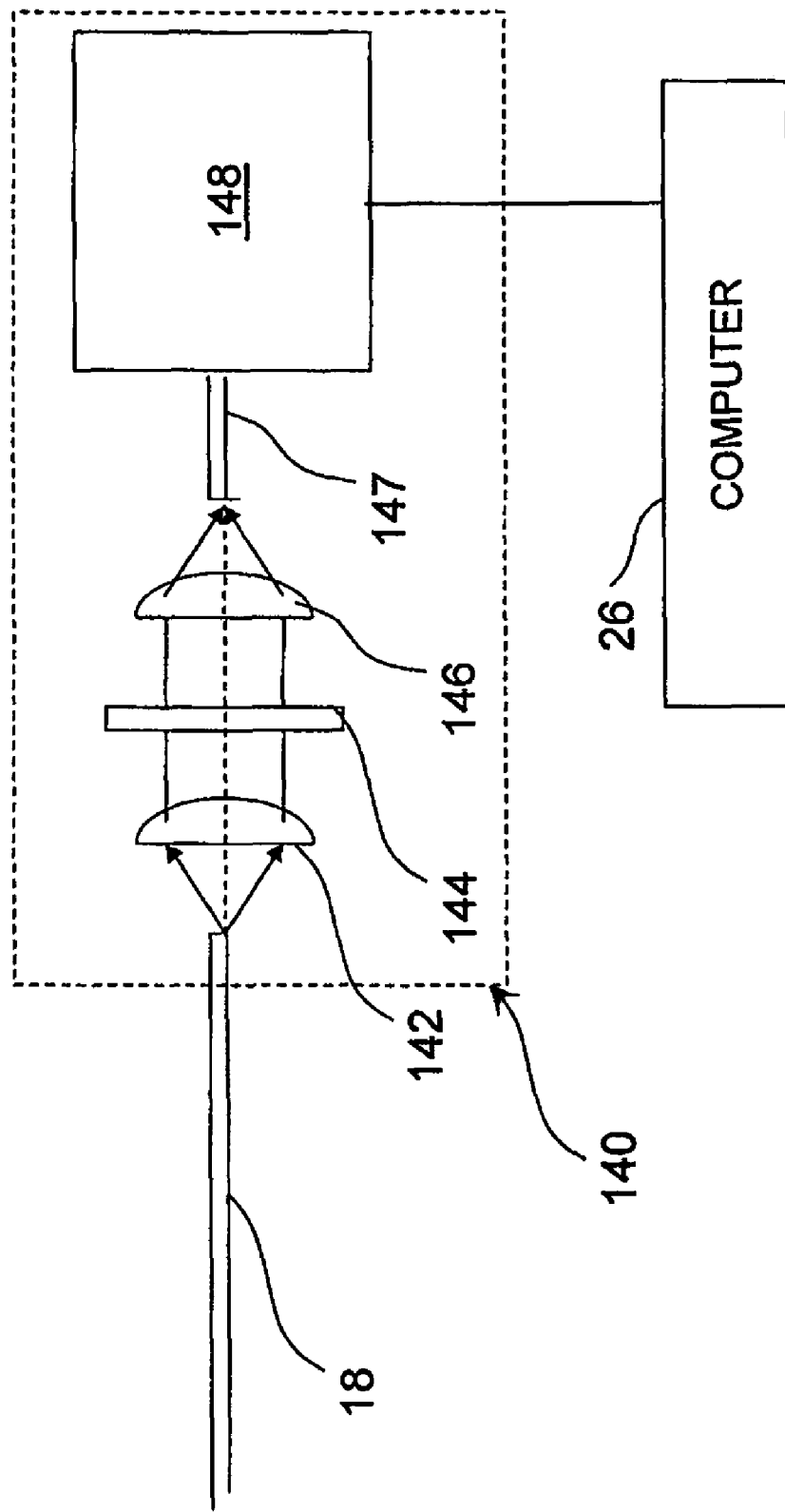
FIG. 7 is a schematic view of an alternative detection system to the detection system of FIG. 6.

FIG. 7 depicts an alternative detection system 140 to the detection system 40 of FIG. 6. The alternative detection system 140 includes a first collimating lens 142 for collecting the light exiting the optical fiber 18; a fluorescence filter 144; an injection lens 146 receiving the light once passed through the filter 144; and a spectrometer 148 having an optic fiber 147 for receiving the light beam concentrated by the injection lens 146. This detection system 140 is suited in the fluorescence study of a homogeneous solution without small bodies and passing through the hole of the optical fiber 18. The filter 144 is used to block out the wavelengths of the source and let fluorescence emanated from the homogeneous solution pass through.

It is to be understood that many other suitable detection systems known by those skilled in the art can be used in view of particular applications, for example, a fiber Bragg grating can be used to separate wavelengths with a single mode optical fiber.

Figure 8A:
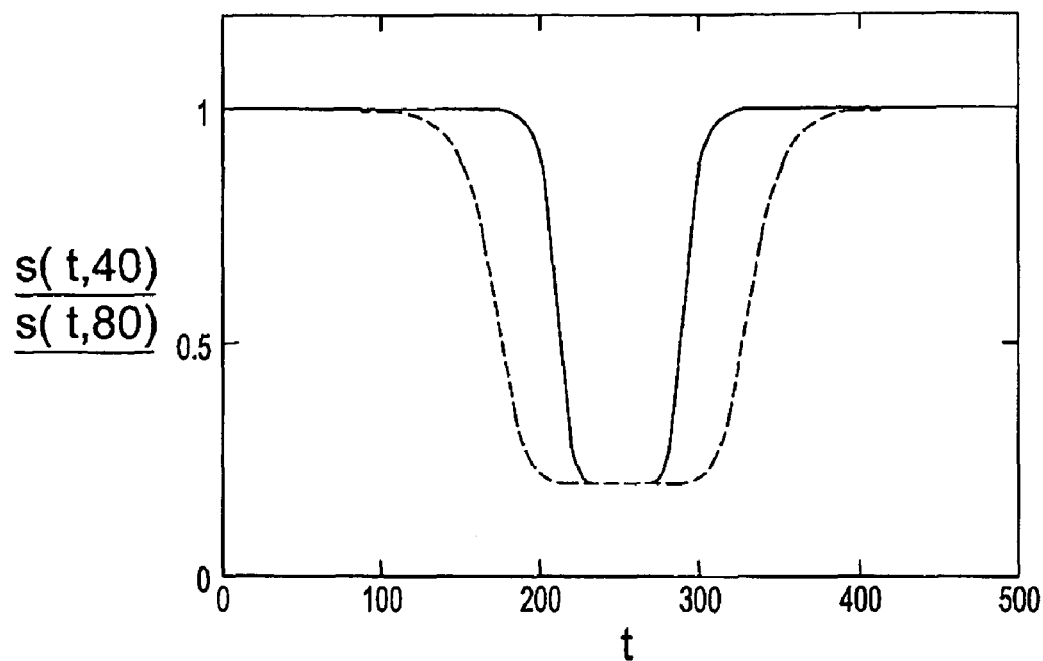
FIG. 8A shows a typical graph illustrating the variation of the quantity of light detected when two bacteria of same size but different lengths are illuminated.
Figure 8B:
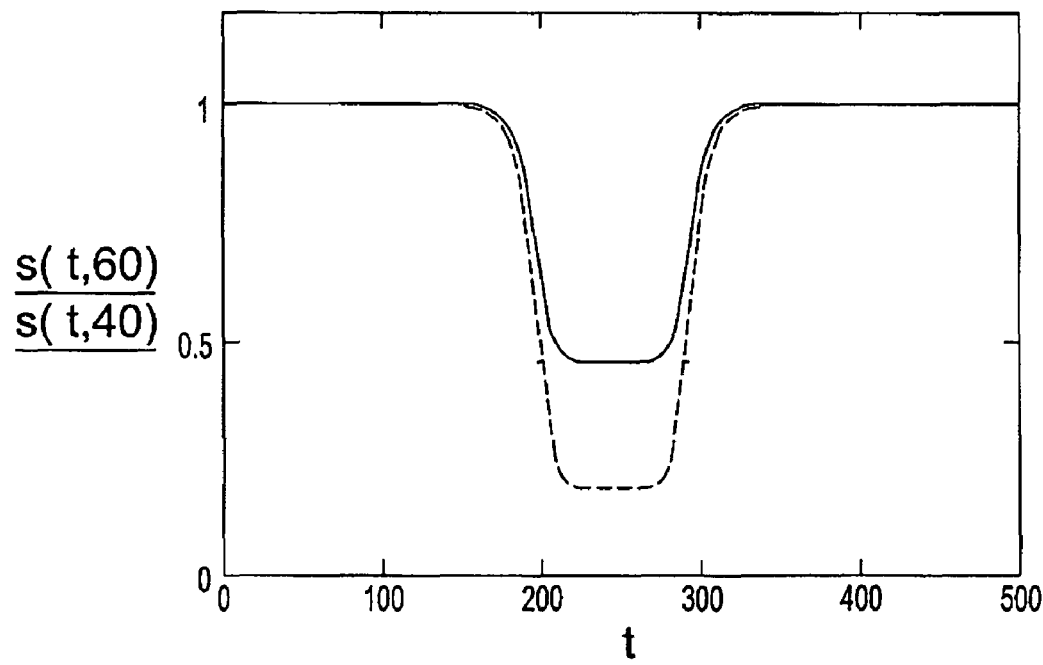
FIG. 8B shows a typical graph illustrating the variation of the quantity of light detected when two bacteria of same length but different sizes are illuminated.

By assessing the detected intensity at wavelength C, the presence of a bacterium in the hole is determined and its size is estimated. Additionally, it is determined whether the bacterium is dead or alive (the vitality status) by assessing the measured intensities at wavelengths A and B. Preferably, the output of photodetector 48C can be connected to an acquisition card of the computer 26. The variation of the electric signal of the photodetector 48C with time is stored in the computer memory during the flow of the fluid medium. Assuming that the size and the length of the bacteria are taken, respectively, parallel and perpendicular to the optical axis of the optical fiber, the normalized electrical signal varies as a function of time and the variation depends on the size and length of the bacteria intersecting the light beam, as shown in FIGS. 8A and 8B. Since the quantity of light scattered depends on the size of the bacteria, the amplitude variation of the electrical signal is indicative of the size of the bacteria. Further, the duration of the amplitude variation is indicative of the length of the bacteria when the flow rate is set at a fixed value. Hence, two bacteria of same size but of different lengths are responsible for the superposed signals illustrated in FIG. 8A, whereas two bacteria of different sizes but of same length are responsible for the superposed signals of FIG. 8B. A relatively simple algorithm can calculate the first derivative of the signal s (t, a), where t and a represent the time and the length of the bacteria respectively, and activate a timer, comparators, and counters to determine the duration and amplitude of the electrical impulses. In this way, an impulsion of given amplitude and given duration would be associated to a bacterium of given size and given length intersecting the light beam. In this preferred example, a single algorithm suffices to indicate the presence, size, and length of the bacterium, and the detection system 40, acquisition card, and computer 26 serve as both a presence detector and a dimension detector. The triple assessment can alternatively be made by two or three algorithms provided in the computer 26 using a single signal and acquisition card, or a separate presence detector and dimension detector, having the corresponding functions, can be used instead. The dimension detector can also be provided as separate size and length detectors. Calibration of the instrument can be done with micro-spheres of known diameter, like it is the case in other commercial flow cytometers.

Figure 8C:
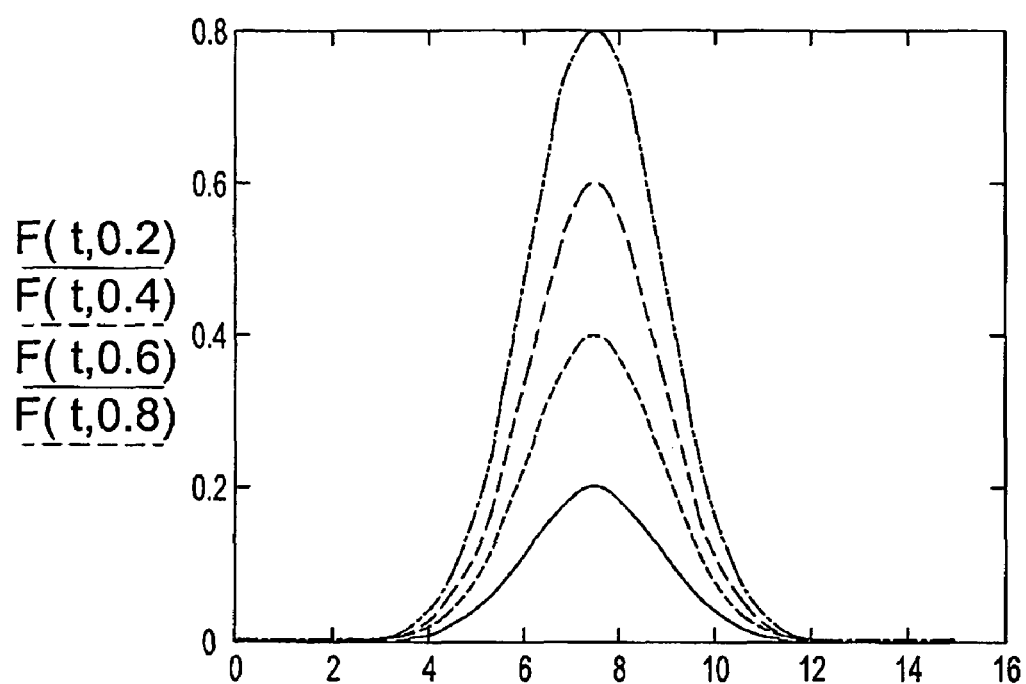
FIG. 8C illustrates the electric pulses produced by the fluorescence of bacteria labeled with fluorophores.

For a living bacterium, the signal acquisition from the output of photodetectors 48C and 48B are practically simultaneous, and the function of detecting status is carried out using both signals. The fluorescence signal F (t, b), where t represents the time, at the exit of photodetector 48B can take the shape of an electric impulse such as depicted in FIG. 8C. For bacteria smaller than the diameter of the optical fiber core, the amplitude b of this signal depends of the number of fluorophores which are attached to the bacteria. If the dyeing of the bacteria is successful, the amplitude of this signal will vary as a function of the size of the bacteria. Therefore, the simultaneous detection of an electrical impulse at the exit of photodetectors 48C and 48B is indicative of the passage of a living bacterium across the light beam in the optical fiber. Similarly, the passage of a dead bacterium is indicated by simultaneous impulses at the exit of photodetectors 48A and

48C. Standard micro-spheres labeled with a fluorochrome of absorption wavelength compatible with the peak wavelength of the light source can be used to calibrate photodetectors 48B and 48A. Preferably, the corresponding algorithm to determine the status is provided in the computer 26, and is done in combination with the dimension and presence determination. However, a separate status detector can be used.

Figure 9:
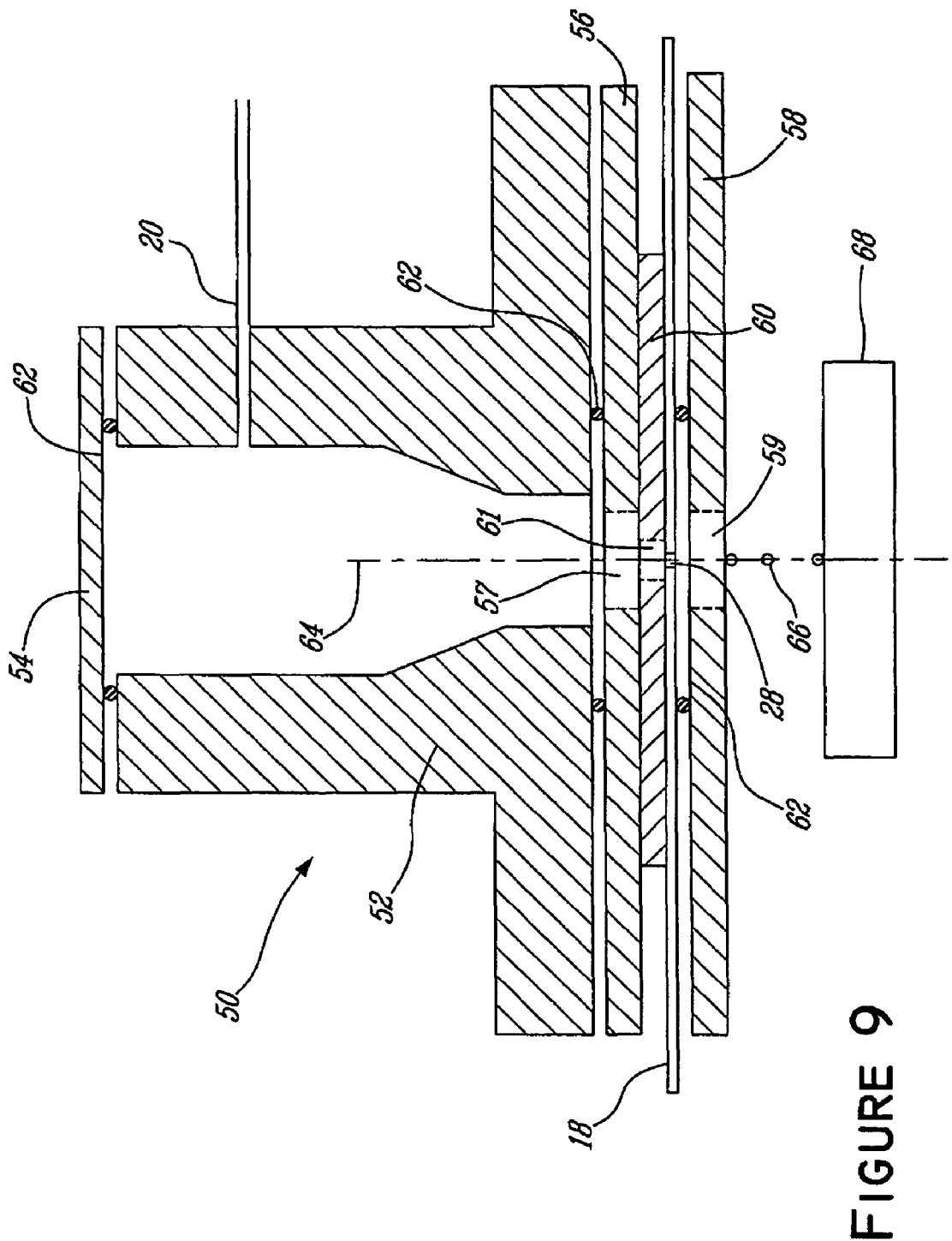
FIG. 9 is a cross-sectional view of a channeling system of the apparatus of FIG. 1.

FIG. 9 shows an exemplary embodiment of the channeling system 50. A container 52 with a cover 54 contains the fluid medium in which the small bodies are held. Pressure is transmitted into the container 52 via the pressure inlet 20. The optical fiber 18 is held between a container plate 56 and protector plate 58 through which coaxial container apertures 57 and protector plate aperture 59 are defined. Preferably, container plate 56 is made of steel, and has a container aperture 57 of 500 μm. A glass plate 60 of 150 μm thickness with an intermediate aperture 61 of a diameter between container aperture 57 and that of the hole 28 in the optical fiber 18 is used between container plate 56 and optical fiber 18 to channel the fluid medium by successively funneling it more precisely into the region of light propagation. Intermediate aperture 61 is preferably of 75 μm diameter, and the portion of the optical fiber 18 having the hole 28 is held and sealed thereagainst by glue applied around intermediate aperture 61. Epotek produces a variety of glues with low autofluorescence that can be used to bond optical elements. A gasket 62 having a diameter approaching 3 mm is preferably used between the optical fiber 18 and protector plate 58. A gasket 62 is also used between container plate 56 and container 52, as well as between container 52 and cover 54. Hence, container aperture 57, protector plate aperture 59, intermediate aperture 61 and hole 28 are coaxially aligned along a channeling axis 64. Once it has passed through the hole 28, the fluid medium 36 creates drops 66 which fall into a recipient 68. The frusto-conical shape of the hole 28, which is shown exaggerated in FIGS. 2 and 3, slightly contributes to the funneling action. The pressure to the channeling system is fed from a pressure tank 22, and is controlled by a computer 26 via a pressure controller 24. Preferably, the pressure tank contains dry air and the computer 26 controls the pressure controller 24 depending on the output light detected by the detection system 40. Any suitable alternative channeling system 50 can be selected and used by those skilled in the art realizing alternative embodiments of the invention. Typically, those realizing alternative funneling systems will select alternatives which ensure precision of entry of the fluid medium in the hole 28.

Figure 10:
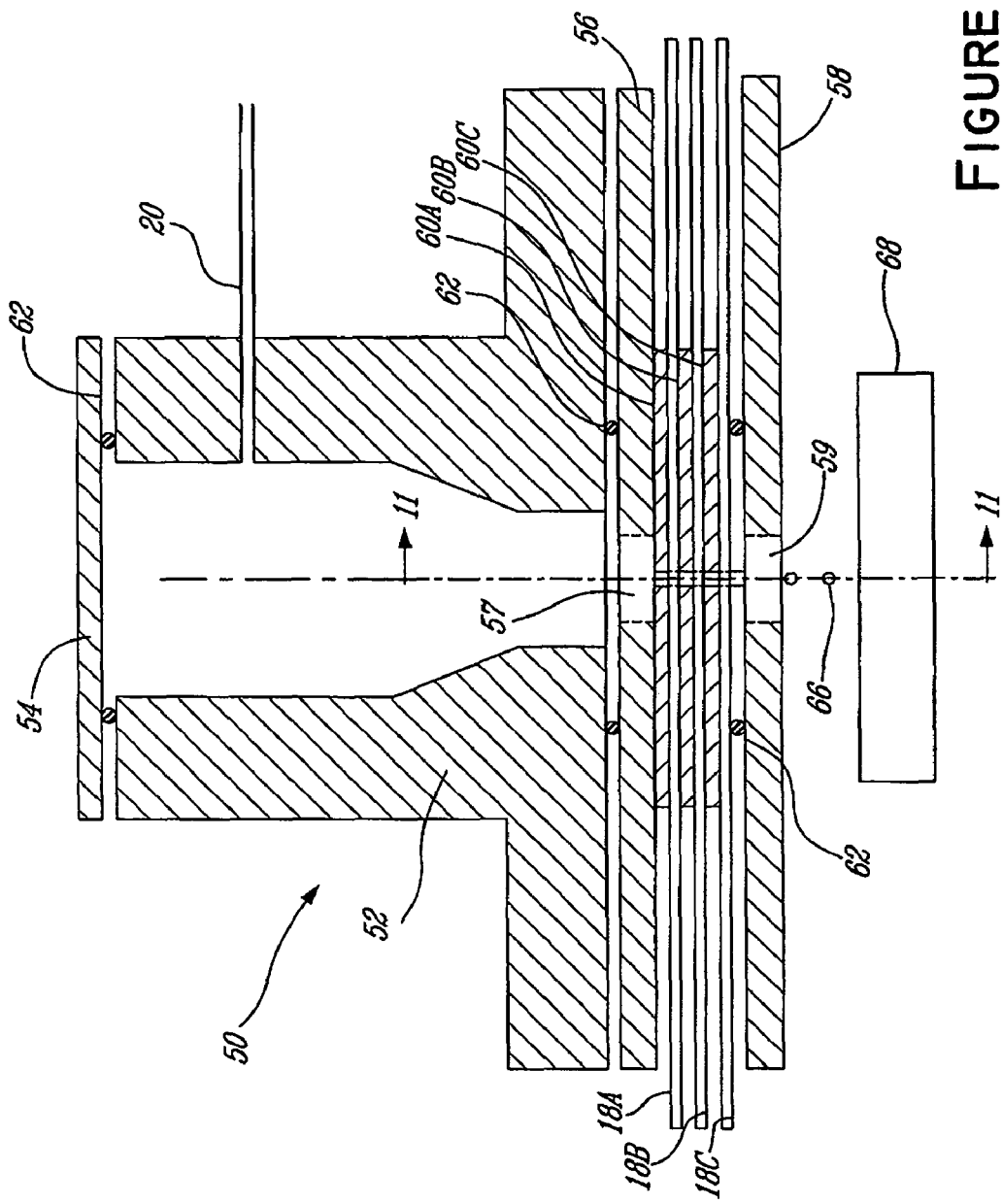
FIG. 10 is a cross-sectional view of an alternative to the channeling system of FIG. 9, adapted to three superposed optical fibers.
Figure 11:
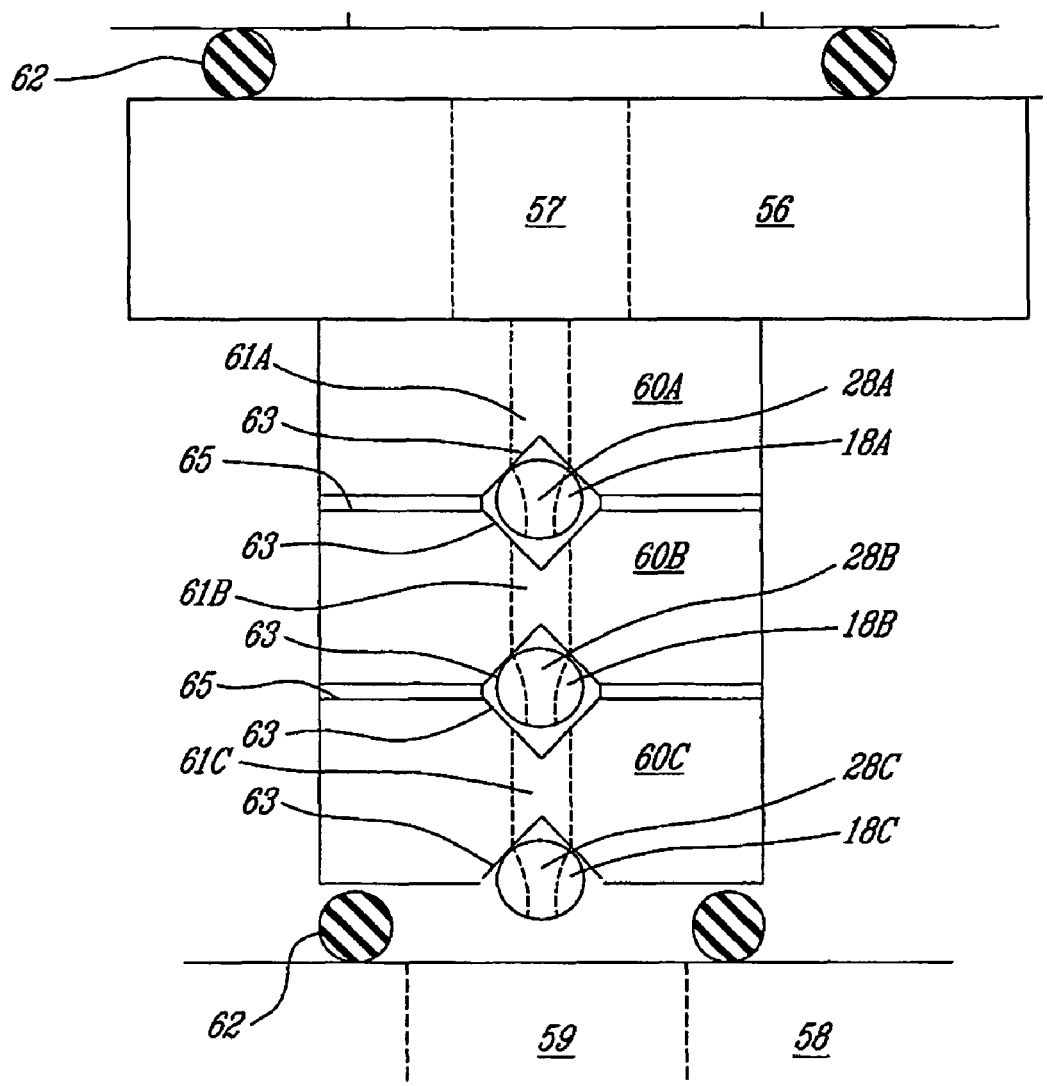
FIG. 11 is a cross-sectional view taken along cross section lines 11-11 of FIG. 10.

FIG. 10 illustrates an alternative to the channeling system where the fluid medium intersects three successive optical fibers 18. Three glass plates 60A, 60B, 60C act as intermediary between the fibers, and between the first optical fiber and the upper plate 56. The funneling action into the successive optical fibers 18A, 18B, 18C is illustrated in FIG. 11 where it is shown that a channel is defined between the container aperture 57, and the aperture 61A in the first glass plate 60A, between first aperture 61A and the hole 28A in the first optical fiber 18A, between the first hole 28A and the second aperture 61B, and successively through the holes in the second and third optical fibers 18B and 18C. The glass plates 60A, 60B, 60C are preferably melted silica lamellae which are made with grooves 63 to make it easier to position the optical fibers relatively to the channel. The successive glass plates 60 are glued together via spacers 65.

Using successive optical fibers provides the following advantages. A light source of a different peak wavelength can be used in each successive optical fiber 18, which allows using fluorochrome dyes with different absorption wavelengths, for example. Further, knowing the distance between the successive fibers, the flow rate of the fluid medium can be measured by adding micro-spheres marked with a specific dye, and measuring the time elapsed between the impulses in the intensity of light detected at the exit of the corresponding fibers. In fact, the impulse detected at the exit of the first optical fiber 18A can be used to trigger a light pulse from the light source of a successive optical fiber. In this application, a pulsating emission LED can thus be used to produce a concentrated pulse of high intensity light directly onto an oncoming bacterium. This can be particularly advantageous when attempting to generate fluorescence outputs which necessitate a high intensity of light. The bacteria will thus receive the high intensity light pulse and the fluorescence signal detected at the exit should be proportionally increased.

Figure 12:
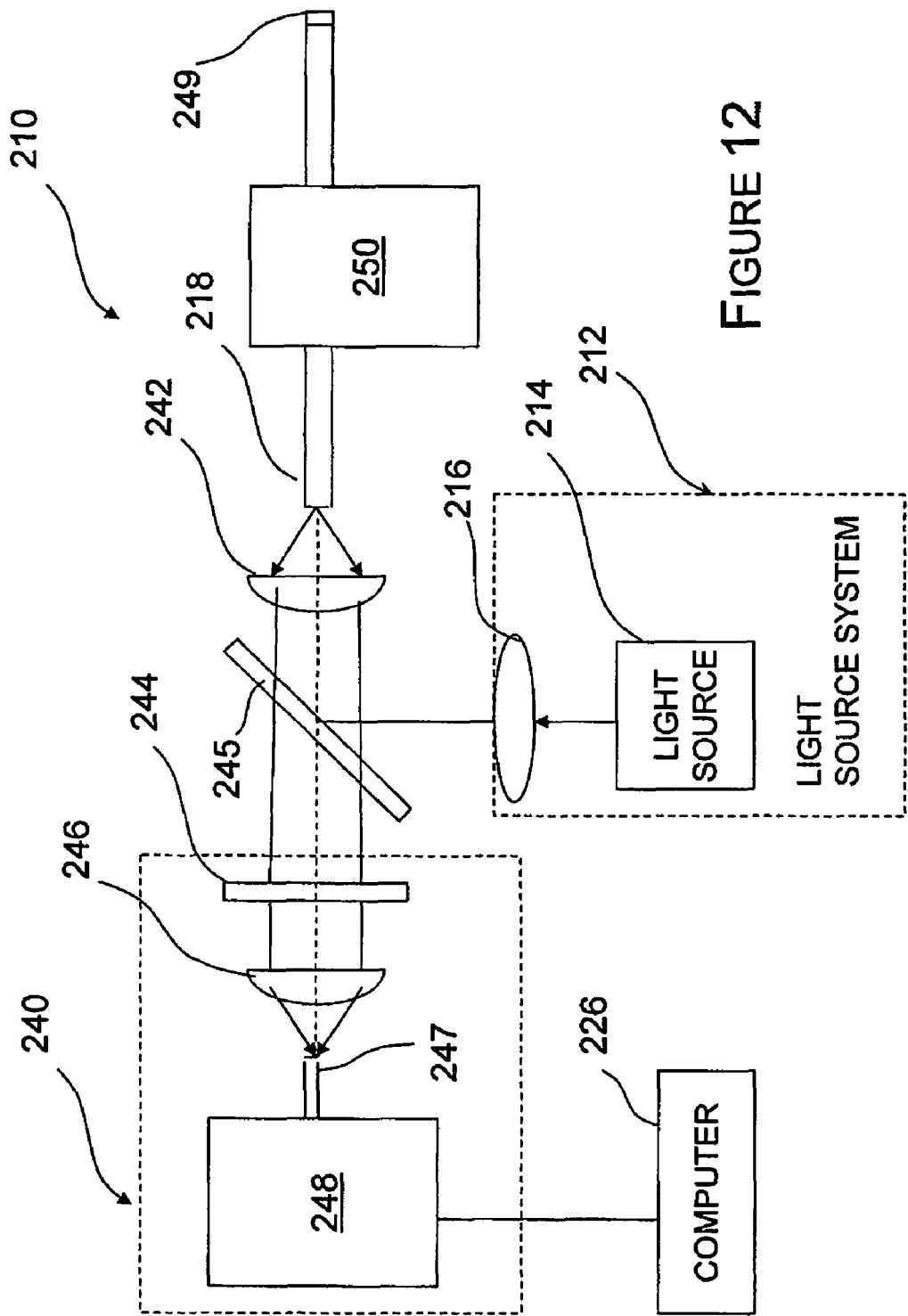
FIG. 12 is a schematic view of an alternative to the apparatus of FIG. 1.

Turning now to FIG. 12, an alternate embodiment to the apparatus described above is shown. Tests have shown that using the apparatus described above, a variation of the optical signal is measured when particles cross the passage in the optical fiber. However, it remains that there are undesirable variations in the electrical signal. These variations are caused, for example, by the passage of particles following different trajectories in the hole of the optical fiber and also by electronic noise, since the quantity of detected light remains relatively low. Hence, to minimize the variations caused by the passage of the particles following different trajectories, a system mounted in reflection instead of a system mounted in transmission can be used as will now be described using reference numerals in the 200 series.

The alternate apparatus 210 also includes a light-source system 212, an optical fiber 218, a channeling system 250 and a detection system 240. However, it is seen that both the light-source system 212 and the detection system 240 are connected to the same end of the optical fiber 218. In particular, a dichroic filter 245 is used. In use, light from the light-source system 212 is reflected by the dichroic filter 245 and fed into the optical fiber 218. The light then crosses an interaction volume in a passageway in the optical fiber where the fluid is channeled by the channeling system 250. The light interacts with the fluid. Fluorescence emitted in the interaction volume will then travel back in the optical fiber 218 and across the dichroic filter 245 to be detected by the detection system. A metallic layer 249 can be used at the other end of the optic fiber 218 to reflect light. Fluorescence emanated in the optical fiber in the direction of the metallic layer will then be reflected back across the hole, out the optical fiber 218 and will also be detected by the detection system 240. Light at a wavelength of that emitted by the light-source system which is reflected back from the metallic layer 249 will be reflected by the dichroic filter 245. This latter example of an alternate configuration is particularly interesting to measure fluorescence of particles.

Figure 13:
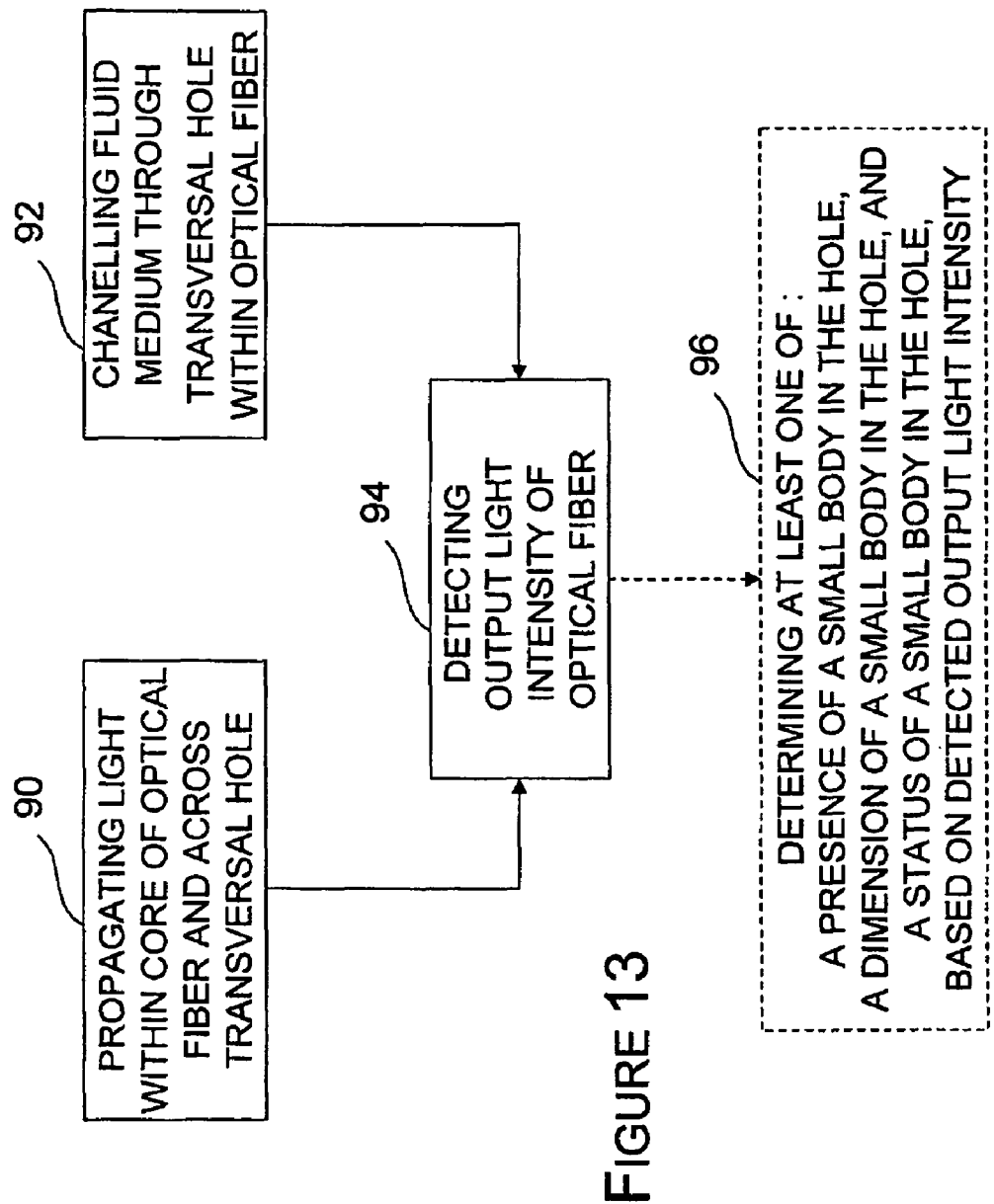
FIG. 13 is a flow chart illustrating the main steps of a method of analyzing small bodies in a fluid medium, in accordance with one other embodiment of the present invention.

FIG. 13 presents a method for analyzing small bodies in a fluid medium in accordance with another embodiment of the present invention. The method includes channeling 92 the fluid medium containing the small bodies in the hole traversing transversally an optical fiber, propagating 90 a light into the core of the optical fiber and across the hole and generating an output light intensity, and detecting 94 the output light intensity. The method may further comprise determining 96 at least one of the following: the presence in the hole of a small body, the size of a small body in the hole and the vitality status of a small body in the hole, based on the detected output light intensity.

The apparatus can be considered as a flow cytometer in which the fluid medium is channeled within the transversal hole of the optical fiber, and the light is guided within the optical fiber and intersects the path of the fluid medium in the hole. The small bodies are analyzed by detecting the output of light exiting the fiber after it has intersected the fluid medium.

Although the preferred embodiment of the invention described referred most specifically to the study of bacteria in water, one skilled in the art will understand that the invention is adapted to study other small bodies in other fluid mediums. For example, alternative small bodies can be cells, other biological specimen, particles in solution, etc., whereas alternative fluid mediums can be other liquids having a relatively low viscosity, like alcohol, milk or blood based liquids. One will also understand that the fluid medium can also alternatively be a gas such as air in which small particles in suspension are studied by crossing a light beam guided within an optical fiber. In this latter case, the channeling system should be sealed. Further, as it was seen above, the system could be used to analyze a homogeneous fluid solution without small bodies. Such a homogeneous fluid preferably includes fluorophores and is studied by the fluorescence it emits and which is guided within the exiting light.

The embodiments of the invention described above are intended to be exemplary only. The scope of the invention is therefore intended to be limited solely by the scope of the appended claims.

What is claimed is:

1. An apparatus for analyzing a fluid, the apparatus comprising:
   an optical fiber with a core extending along a longitudinal optical axis of the optical fiber for a propagation of light along the optical axis, said core being solid except for a transversal passageway traversing the optical fiber directly through the optical axis including through said core, the passageway being a hole traversing the optical fiber in a substantially orthogonal direction relative to said optical axis of the optical fiber and having at least a portion with a taper shape;
   a channeling system adapted to channel the fluid through the passageway;
   a light source system optically coupled to the optical fiber to propagate light in the solid core of the optical fiber, and across the passageway; and
   a light detection system optically coupled to the optical fiber for detecting an intensity of the light exiting the fiber after having propagated across the fluid in the passageway.

2. The apparatus of claim 1, wherein said fluid contains small bodies.

3. The apparatus of claim 2, wherein the small bodies are biological specimens.

4. The apparatus of claim 3, wherein the small bodies are bacteria.

5. The apparatus of claim 1, wherein said fluid is a homogeneous solution including fluorophores.

6. The apparatus of claim 1, wherein the optical fiber is a multimode optical fiber having a core diameter of 62.5 µm, and the hole has a diameter between 10 µm and 50 µm.

7. The apparatus of claim 2, wherein the light detection system further comprises a presence detector for detecting a presence of a small body in the fluid in the hole based on an impulse of the detected exiting light intensity.

8. The apparatus of claim 2, wherein the light detection system further comprises a dimension detector for determining at least one of a size and a length of the small body based respectively on at least one of an amplitude and a duration of an impulse in the detected exiting light intensity.

9. The apparatus of claim 2, wherein the light detection system further comprises a status detector for detecting a fluorescence intensity emitted by a biological specimen in the hole, whereby a vitality status of the biological specimen is determined by an impulse in the fluorescence intensity detected.

10. The apparatus of claim 1 wherein the light source system comprises a UV source and the fluid includes fluorophores.

11. The apparatus of claim 1 wherein the light detection system is adapted to detect light intensity at three different wavelengths.

12. The apparatus of claim 1 wherein the light detection system has a collimation lens receiving light exiting the optical fiber, a diffraction grating receiving the collimated light and diffracting it, and at least one focusing lens and photodetector assembly disposed at a predetermined angle to said diffraction grating for detecting an intensity of light of a predetermined wavelength diffracted by the diffraction grating.

13. The apparatus of claim 1 wherein the light detection system has an optical fiber spectrograph, a collimation lens for receiving light exiting the optical fiber, a filter for filtering the wavelengths of exiting light corresponding to the light source system, an injection lens for injecting the filtered light into the optical fiber spectrograph.

14. The apparatus of claim 1 wherein the channeling system comprises a container of the fluid and a container aperture at least partly coaxial with the passageway, and an intermediate plate between the optical fiber and the container having an intermediate aperture of a size intermediate between that of the passageway and that of the container aperture, the intermediate aperture being disposed along the direction of the passageway, whereby the fluid is successively funneled into the passageway through the container and intermediate apertures.

15. The apparatus of claim 14 wherein the channeling system further comprises a pressure controller for controlling a pressure in the container.

16. The apparatus of claim 1 wherein the optical fiber is a double clad optical fiber.

17. The apparatus of claim 1 wherein the optical fiber further comprises a second core.

18. A method for analyzing a fluid, the method comprising:
   channeling the fluid through a transversal passageway traversing through a core extending along a longitudinal optical axis of an optical fiber and which is solid except for the passageway, the passageway being a hole traversing the optical fiber in a substantially orthogonal direction relative to said optical axis of the optical fiber and having at least a portion with a taper shape, said optical axis being an axis for a propagation of light in said optical fiber;
   propagating light into the core of the optical fiber and across the passageway and generating a light output; and
   detecting an intensity of the light output.

19. The method as claimed in claim 18, wherein small bodies are provided in said fluid, further comprising determining a presence of a small body in the passageway by detecting an impulse in the detected output light intensity.

20. The method as claimed in claim 18, wherein small bodies are provided in said fluid, further comprising determining a dimension of a small body in the passageway by deducing the size and length of the small body from the amplitude and duration, respectively, of an impulse in the detected output light intensity.

21. The method as claimed in claim 18, wherein small bodies are provided in said fluid, further comprising determining a vitality state of a small body in the hole as being one of alive and dead by detecting an intensity of a spectral portion of the light output generated by a fluorescence emitted by the small body.

22. The method as claimed in claim 18 wherein the optical fiber has a second core and the light is propagated in both cores thus generating two light outputs, further comprising analyzing the light intensity emanating from the light outputs using an interferogram.

23. A flow cytometer for analyzing a fluid by channeling the fluid and intersecting the channeled fluid with light for interaction therewith and to be detected thereafter, characterized in that: the fluid is channeled through a transversal hole defined substantially orthogonally relative to a longitudinal optical axis of an optical fiber, said optical fiber has a core which is solid except for said hole and said hole has at least a portion with a taper shape, said optical axis being an axis for the propagation of light in said optical fiber, and the light is guided longitudinally within the optical fiber along said optical axis and intersects the channeled fluid.

* * * * *